United States Patent [19]
Ho et al.

[11] Patent Number: 5,502,165
[45] Date of Patent: Mar. 26, 1996

[54] PROCESS FOR PEPTIDE SEGMENT CONDENSATION

[75] Inventors: Guo-Jie Ho, Rahway; David A. Mathre, Skillman; Zhiguo Song, Edison; Khateeta Emerson, Iselin, all of N.J.

[73] Assignee: Merck & Co., Inc., Rahway, N.J.

[21] Appl. No.: 222,767

[22] Filed: Apr. 4, 1994

[51] Int. Cl.$^6$ .................... C07C 231/02; C07K 1/08
[52] U.S. Cl. .................... 530/341; 530/338; 530/339; 562/443; 562/553; 564/138; 564/164; 564/193; 564/198
[58] Field of Search .................... 530/341, 339, 530/338; 564/138, 164, 193, 198; 562/443, 553

[56] References Cited

U.S. PATENT DOCUMENTS

| | | | |
|---|---|---|---|
| 3,870,694 | 3/1975 | Fujino et al. | 530/341 |
| 4,755,591 | 7/1988 | Konig et al. | 530/338 |
| 5,166,394 | 11/1992 | Breipohl et al. | 558/384 |

FOREIGN PATENT DOCUMENTS

| | | | |
|---|---|---|---|
| 160415 | 7/1983 | German Dem. Rep. | 530/341 |
| 259597 | 11/1987 | Japan . | |

OTHER PUBLICATIONS

Nozaki, S. et al., Chem. Lett. 1977, 1057–1058, entitled, Rapid Peptide Synthesis in Liquid Phase. Preparation of Angiotension II as an Example.

Nozaki, S. & Muramatsu, I., Bull. Chem. Soc. Japan, 1982, 55,2165–2168, entitled, Rapid Peptide Synthesis in Liquid Phase, Preparation of Angiotension II and Delta–sleep–inducing Peptide by the "Hold–in–Solution" Method.

Schneider, C. H. and Wirz, W., Helv. Chim. Acta, 1972, 55, 1062–1074, entitled, Antigen Synthesis: The Preparation of Selected Dodecapeptide Carriers with Systematically Altered Structures by a Two–Phase Method.

Sheehan, J. C., et aL., J. Am. Chem. Soc., 1965, 87, 2492–2493, entitled, A Rapid Synthesis of Oligopeptide Derivatives Without Isolation of Intermediates.

Fujino, M. et al., Chem. Pharm Bull., 1974, 22(8), 1857–1863, entitled, The Use of N–Hydroxy–5–norbornene–2,3–dicarboximide Active Esters in Peptide Synthesis.

Carpino, L. A., J. Am. Chem. Soc., 1993, 115, 4397–4398, entitled, 1–Hydroxy–7–azabenzotriazole. An Efficient Peptide Coupling Additive.

Primary Examiner—Jeffrey E. Russel
Attorney, Agent, or Firm—Mary A. Appollina; Melvin Winokur

[57] ABSTRACT

The present invention is drawn to a process for forming an amide bond linkage comprising reacting a carboxylic acid and an amine in a two-phase mixture of water and an organic solvent selected from an oxygenated organic solvent or an aromatic solvent in the presence of a coupling reagent and an additive. This process is useful for making ubiquitous amides and polypeptides having various biological activities.

9 Claims, No Drawings

PROCESS FOR PEPTIDE SEGMENT CONDENSATION

FIELD OF THE INVENTION

The present invention provides a process for the preparation of oligopeptides in high yields with low racemization. The process is also applicable to amide formation in general. More particularly, the process of the present invention employs a two-phase solvent mixture along with a coupling reagent and an additive to effect the amide linkage in high yield with low racemization.

BACKGROUND OF THE INVENTION

In the past, N-ethyl-N'-[3-(dimethylamino)propyl]carbodiimide hydrochloride (EDC) was used as the coupling reagent during amide formation. Typically, the EDC-mediated amide formation reactions were carried out in a polar solvent such as acetonitrile or dimethylformamide. The work-up involving these solvents was difficult and time consuming, requiring repetitive back extractions. Very often, peptides prepared by this procedure contained certain amount of the epimer (generated by racemization of the carboxyl fragment). Thus, one of the major challenges in peptide synthesis is the prevention of racemization.

The addition of N-hydroxy compounds, such as 1-hydroxybenzotriazole (HOBT), suppresses side reactions and reduces racemization. In certain circumstances, however, racemization still occurs, even in the presence of the additive. Recently, it has been shown that 1-hydroxy-7-azabenzotriazole (HOAT) is also effective as an additive in preserving chiral integrity during peptide coupling reactions. [Carpino, L. A., *J. Am. Chem. Soc.*, 1993, 115, 4397–4798]. A certain amount of racemization is still inevitable, however, even with this new additive.

A two-phase approach for oligopeptide synthesis has been reported in which the coupling reactions were carried out in dichloromethane using the water soluble EDC as the coupling reagent. The side products of the reactions were them removed by aqueous extractions after the coupling was complete. [Sheehan, J. C. et al., *J. Am. Chem. Soc.*, 1965, 87, 2492–2493]. This method has been employed in the active ester coupling starting with the N-hydroxysuccinimide esters. [Schneider, C. H.; Wirz, W.; *Helv. Chim. Acta*, 1972, 55, 1062–1074]. The EDC-mediated coupling reaction in dichloromethane sometimes still resulted in considerable extent of racemization, however, even with HOBT as the additive.

A "hold-in-solution" method for oligopeptide synthesis, in which the reaction was carried out at room temperature in a two-phase mixture of dichloroethane and water using EDC as the coupling reagent and HOBT as the additive, has been reported by Nozaki, et al. The extent of racemization was not reported, however, and the yields were not optimized. Furthermore, only N-Boc-amino acids were used for the peptide elongation, and it is known that the Boc protecting group suppresses the racemization during peptide coupling. [Nozaki, S., et al., *Chem. Lett.* 1977, 1057; Nozaki, S.; Muramatsu, I., *Bull. Chem. Soc. Japan*, 1982, 55, 2165.] Thus, a need remains for a method of peptide segment condensation which provides easier work-up, higher recovery yields and less racemization; more specifically, a general method of peptide segment condensation which does not require the use of Boc protected amino acid starting materials in order to obtain low racemization would be highly desirable. In addition, a coupling process which does not require handling or disposal of halogenated solvents would result in reduced environmental problems; these environmental concerns become increasingly important when the peptide coupling reaction is done on a large scale.

SUMMARY OF THE INVENTION

The instant invention involves a process for forming an amide linkage comprising reacting an acid and an amine, in the presence of a coupling reagent and an additive, in a bi-phasic mixture of water and an organic solvent selected from an oxygenated organic solvent or an aromatic solvent.

In one embodiment of the invention is the process wherein the organic solvent is selected from an organic ester, an ether or an aromatic.

In a class is the process wherein the organic solvent is selected from isopropyl acetate, methyl t-butyl ether or toluene.

In a subclass is the process wherein the organic solvent is isopropyl acetate.

Illustrative of the invention is the process wherein the coupling reagent is selected from the group consisting of EDC, DCC and diisopropylcarbodiimide.

A further illustration of the invention is the process wherein the coupling reagent is EDC.

Further illustrating the invention is the process wherein the additive is selected from the group consisting of 2-hydroxypyridine N-oxide, 1-hydroxybenzotriazole, N-hydroxysuccinimide, 1-hydroxy-7-azabenzotriazole and endo-N-hydroxy-5-norbornene-2,3-dicarboximide.

Exemplifying the invention is the process wherein the additive is 2-hydroxypyridine-N-oxide.

An example of the invention is the process wherein the acid and the amine are protected amino acids.

Further exemplifying the invention is the process wherein the acid is a protected amino acid selected from valine or phenylglycine.

An additional example of the invention is the process wherein the reaction is carried out at a temperature range of about 0° to 5° C.

Specifically exemplifying the invention is the process comprising the additional step of isolating the amide product.

In a second embodiment of the invention is the process wherein said acid does not encompass

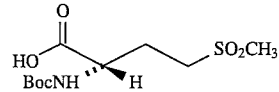

and said base does not encompass

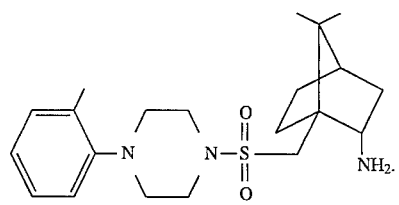

Some abbreviations that appear in this application are as follows:

ABBREVIATIONS

| Designation | |
|---|---|
| | Protecting Group |
| ALLOC | allyloxycarbonyl |
| BOC (Boc) | t-butyloxycarbonyl |
| CBZ (Cbz) | benzyloxycarbonyl (carbobenzoxy) |
| S-MOC | fluorenylmethoxycarbonyl |
| TBS (TBDMS) | t-butyl-dimethylsilyl |
| | Activating Group |
| Ts or tosyl or tosylate | p-toluenesulfonyl |
| Ns or nosyl or nosylate | 3-nitrobenzenesulfonyl |
| Tf or triflyl or triflate | trifluoromethanesulfonyl |
| Ms or mesyl or mesylate | methanesulfonyl |
| | Coupling Reagent |
| BOP reagent | benzotriazol-1-yloxytris(dimethyl-amino)phosphonium hexafluoro-phosphate |
| BOP-Cl | bis(2-oxo-3-oxazolidinyl)phosphinic chloride |
| DCC | dicyclohexylcarbodiimide |
| EDC | 1-ethyl-3-(3-dimethylaminopropyl) carbodiimide hydrochloride |
| | Other |
| BOC-ON | 2-(tert-butylcarbonyloxyimino)-2-phenylacetonitrile |
| (BOC)$_2$O (BOC$_2$O or Boc$_2$O) | di-t-butyl dicarbonate |
| n-Bu$_4$N$^+$F$^-$ | tetrabutyl ammonium fluoride |
| nBuLi (n-Buli) | n-butyllithium |
| (S)-CSA | (1S)-(+)-10-camphorsulfonic acid |
| DI | deionized |
| DIEA or DIPEA | diisopropylethylamine |
| DMAP | dimethylaminopyridine |
| DME | dimethoxyethane |
| DMF | dimethylformamide |
| Et$_3$N | triethylamine |
| EtOAc | ethyl acetate |
| h | hour(s) |
| IPA | 2-propanol |
| i-PrOAc or IPAC | isopropyl acetate |
| KF | Karl Fisher titratation for water |
| LDA | lithium diisopropylamide |
| L-PGA | (L)-pyroglutamic acid |
| r.t. | room temperature |
| TFA | trifluoroacetic acid |
| THF | tetrahydrofuran |
| TLC | thin layer chromatography |

DETAILED DESCRIPTION OF THE INVENTION

The instant invention encompasses a process for preparing oligopeptides in high yields with low racemization according to the following reaction scheme.

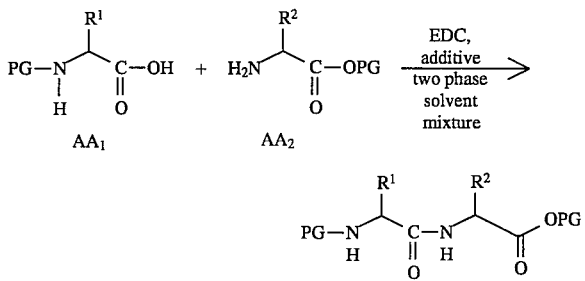

wherein PG is a protecting group and $R^1$ and $R^2$ are amino acid side chains. This method is particularly useful in cases where the carboxy component is especially susceptible to racemization.

More generally, the instant process can be used to form ubiquitous amides having a variety of biological activities. For example, the instant process has been employed to form the amide linkage in the synthesis of the oxytocin receptor antagonist 1-((7,7 -Dimethyl-2-endo-((2S)-amino-4-(methylsulfonyl)-butyramido)bicyclo(2.2.1)heptan-1-yl)methanesulfonyl)-4-(2-methylphenyl)piperazine, designated herein as "Compound A," which is described in European Patent Application EP 0 532 097, published Mar. 17, 1993.

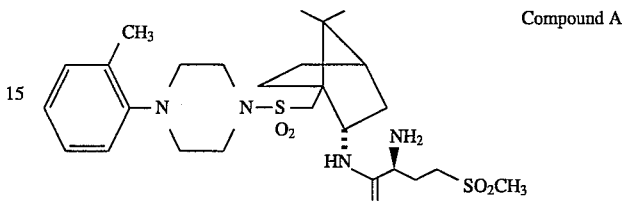

Compound A

In addition, the amide linkage in the fibrinogen receptor antagonist, [3(R)-(−)-[2-(Pyridin-4-yl)ethyl]-2-piperidon-1-yl]acetyl-3(R)-methyl-β-alanine, designated herein as "Compound B," has also been formed using the instant process.

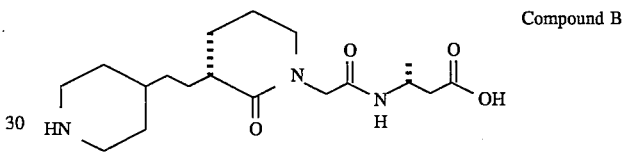

Compound B

Compound B, and its use as a fibrinogen receptor antagonist, is described in European Patent Application EP 0 512 831, published Nov. 11, 1992.

In the instant two-phase procedure for forming an amide linkage, the reactions are carried out in a solvent mixture of water and an immiscible organic solvent (1:1, v/v) using equimolar amounts of the acid and the amine components and the additive, with a 10–15% molar excess of the coupling reagent. Good yields and low racemization are obtained when the reaction is run at a temperature range of about 0° to 5° C., however, a wide range of temperature can be explored depending on the substrates. For example, the reaction can be carried out at room temperature as shown in Example 4 on pages 39–40. A variety of organic solvents are suitable for use in the instant process, so long as the solvent is immiscible in water. Examples of organic solvents which can be used include halogenated hydrocarbons (e.g., chloroform, dichloromethane, dichloroethane), oxygenated organic solvents and aromatics (e.g., toluene). Oxygenated organic solvents which can be utilized include ethers (e.g., diethyl ether, methyl tertiary-butyl ether), esters (e.g., ethyl acetate, isopropyl acetate) and higher molecular weight alcohols which are not miscible with water (e.g., starting with n-butanol and higher). Isopropyl acetate, methyl t-butyl ether and toluene are preferred solvents in the instant two-phase coupling process. Isopropyl acetate is particularly preferred.

Coupling reagents are substances which effect carboxyl activation and dehydration thereby promoting peptide bond formation. That is, coupling reagents are those reagents which condense the carboxylic acid and amine to form an amide. Examples of coupling reagents which can be employed in the instant process include EDC, dicyclohexylcarbodiimide (DCC) and diisopropylcarbodiimide. Preferably, a water soluble coupling reagent such as EDC is used. Addition of an auxiliary nucleophile as the additive has been found to reduce racemization during formation of the amide linkage (i.e., peptide bond formation). An additive is a compound which, when added to the coupling reaction acts as a catalyst, resulting in higher yields and less racemization of the peptides. Various N-hydroxy derivatives such as 2-hydroxypyridine-N-oxide (HOPO), 1-hydroxybenzotrizole (HOBT), N-hydroxysuccinimide (HOSU), 1-hydroxy-7-azabenzotriazole (HOAT) and endo-N-hydroxy-5-norbornene-2,3-dicarboximide (HONB) can be used as the additive in the two-phase coupling reactions. HOPO is the preferred additive in the instant two-phase system.

One skilled in the art will appreciate that although the instant process is suitable for forming any amide linkage, carboxylic acid components and amine components containing additional reactive functional groups will need to be protected on these additional non-reacting functional groups. Moreover, the skilled artisan will recognize that a vast number of protective groups are available and suitable for use in such instances. See Greene, T. W.; Wuts, P.G.M., Protective Groups in Organic Synthesis (2d ed. 1991). For example, when the instant process is utilized to prepare a dipeptide from two amino acids, urethane based protecting groups such as t-BOC, CBz, ALLOC and S-MOC can be used to protect the non-reacting amine component, while benzyl or alkyl esters (e.g., methyl ester, t-butyl ester) can be used to protect the non-reacting carboxy component.

In one embodiment of the present invention, the reactions were carried out in a solvent mixture of dichloromethane or isopropyl acetate (i-PrOAc) and water (1:1, v/v) using equimolar amounts of the N-acetylamino acid and the amino acid benzyl ester components and the additive, with a 10–15% molar excess of EDC as the coupling reagent.

N-Acetylamino acids were chosen for this study since the acetyl group lacks the ability to suppress racemization, and it presumably mimics an adjoining peptide amide unit. This method is also suitable for segment condensation of oligopeptides. Some protected tripeprides have been prepared with very low racemization. The results of the coupling reactions in dichloromethane/water and in i-PrOAc/water are shown in Tables I and II, respectively. For comparison, results for reactions in DMF are also listed in Table III.

Various N-hydroxy derivatives can be used as the additive in the two-phase coupling reactions, such as HOPO, HOBT, HOAT, HONB and HOSU. In the absence of an additive, the coupling reactions in the two-phase mixture generally resulted in low yields (<50%) and extensive racemization (up to 15–30% of the d,l isomer formed). In the dichloromethane/water mixture, HOBT, HOAT and HOPO showed significant effects on coupling efficiency and racemization suppression (Table I). On the other hand, HOBT and HOAT were less effective in reducing racemization in i-PrOAc/water because of poor solubility in this mixture (Table II), even though high yields were still obtained. HONB, readily soluble in i-PrOAc/water, appears to be an effective additive for reactions in this solvent mixture (but not as effective as HOPO). However, HOSU generally afforded the peptides in low yields with significant amounts of side products (detected by HPLC).

Reactions carried out in the two-phase mixtures generally afforded yields comparable to those in DMF with HOBT as the additive but, more importantly, with significantly less racemization. In addition, the two-phase procedure also provides a more convenient work-up than those reactions using DMF as the solvent, and consequently, higher recovery yields were generally obtained. This procedure therefore allows an efficient preparation of large quantities of oligopeptide segments.

As shown in Tables I and II, the racemization-suppressing effect of the two-phase coupling system becomes very significant in cases involving valine or phenylglycine as the acid component, since it is known that coupling reactions of these amino acids are very sensitive towards racemization (Table III). However, the low racemization observed in the two-phase reaction is not only due to the low polarity of the organic solvent, since coupling reactions in dichloromethane gave higher racemization (Table I, entries 4, 6, 8 and 11).

Experimental

All amino acid derivatives were purchased from Sigma, except for Z-phenylglycine (Bachem). All additives (HOBt, HONB, HOPO, and HOSU) were obtained from Aldrich except HOAT (test sample from Millipore). EDC was purchased from JBL Scientific. HPLC analyses were carried out using a Zorbax C18 column (4.6×250 mm) or an Inertsil ODS-2 column (4.6×250 mm) on a Hewlett-Packard 1050 system under the conditions (methanol/water as the eluting solvent, $\lambda$=220 nm) similar to those described by Miyazawa, et al., *Int. J. Peptide Protein Res.*, 1992, 39, 237, unless otherwise noted. The retention times of the diastereomeric peptides were determined by comparing with those of the racemic amino acid coupled products.

EXAMPLE 1

General Procedure for Two-Phase Peptide Coupling Reactions

Preparative run: To a solution of the amino acid benzyl ester ($AA_2$, 4 mmol) in 40 mL of dichloromethane (or i-PrOAc) was added sequentially water (40 mL), the acetylamino acid ($AA_1$, 4 mmol) and the additive. The mixture was then cooled in an ice bath to 0°–5° C. and EDC (4.4 mmol) was added. The resulting mixture was then stirred for 24–40 hr. at 0°–5° C. Aqueous hydrochloric acid (2M, 10 mL) was added and the layers partitioned. The organic phase was further washed sequentially with aqueous hydrochloric acid (0.5M, 20 mL), brine (20 mL), aqueous sodium bicarbonate (1M, 2×20 mL) and brine (2×20 mL). The organic phase was then dried over sodium sulfate, filtered, and concentrated to dryness.

Analytical run: The reaction was carried out in 0.2 mmol scale in 4 mL of 1:1 dichloromethane/water (or i-PrOAc/water). At the end of the reaction, the mixture was diluted with 60:40 MeOH/$H_2O$ (v/v) to 50 mL and assayed by HPLC.

TABLE I

| Coupling Reaction in Dichloromethane/water Mixture[a,b] | | | | |
|---|---|---|---|---|
| entry | $AA_1$ | $AA_2$[c] | additive | yield % | d,l isomer % |
| 1 | Ac—Val | ValOBn | HOBT | 93 | 0.1 |
| 2 | Ac—Val | ValOBn | HOPO | 93 | 0.2 |
| 3 | Ac—Val | LeuOBn | HOBT | 99 | 0.3 |
| 4[d] | Ac—Val | LeuOBn | HOBT | 92 | 2.8 |
| 5 | Ac—Val | LeuOBn | HOPO | 94 | 0.1 |
| 6[e] | Ac—Val | LeuOBn | HOPO | 84 | 2.2 |
| 7 | Ac—Val | PheOBn | HOBT | 95 | 0.4 |
| 8 | Ac—Val | PheOBn | HOPO | 95 | 0.3 |
| 9 | Ac—Phe | LeuOBn | HOBT | ~100 | 0.2 |
| 10 | Ac—Phe | LeuOBn | HOPO | ~100 | 0.3 |
| 11 | Ac—Phe | ValOBn | HOBT | 95 | 0.2 |
| 12 | Ac—Phe | ValOBn | HOPO | 92 | 0.6 |
| 13 | Z—Phg | LeuOBn | HOBT | 88 | ~0.07 |
| 14[d] | Z—Phg | LeuOBn | HOBT | 93 | 0.6 |
| 15 | Z—Phg | LeuOBn | HOPO | 94 | N.D.[f] |
| 16 | Z—Phg | ValOBn | HOPO | 99 | N.D.[f] |
| 17[d] | Z—Phg | ValOBn | HOAT | 98 | 0.2 |

TABLE I-continued

Coupling Reaction in Dichloromethane/water Mixture[a,b]

| entry | AA$_1$ | AA$_2$[c] | additive | yield % | d,l isomer % |
|---|---|---|---|---|---|
| 18 | Z—Phg | ValOBn | HOAT | 97 | N.D.[f] |
| 19 | Z—Gly—Val | ValOBn | HOBT | 97 | N.D.[f] |
| 20 | Z—Gly—Val | ValOBn | HOPO | 92 | N.D.[f] |
| 21 | Z—Gly—Val | ValOBn | HOAT | 95 | N.D.[f] |

[a] Abbreviations: AA$_1$, AA$_2$ = amino acid or dipeptide fragment; Ac = acetyl; Z = (benzyloxy)carbonyl; OBn = benzyloxy.
[b] Reactions (0.2 mmol scale) were carried out in 4 mL of 1:1 dichloromethane/water (v/v) with 1 eq. of the additive using 1.1 eq. of EDC, at 0–5° C. for 24–40 hrs. then assayed by HPLC, see experimental.
[c] Solution of the amino acid benzyl ester solution in dichloromethane.
[d] Reaction is dichloromethane only, no water added.
[e] Reaction in dichloromethane only, HOPO is not completely dissolved.
[f] Not detected, <0.05%.

TABLE II

Coupling Reactions in Isopropyl Acetate/Water Mixture[a,b]

| entry | AA$_1$ | AA$_2$[c] | additive | yield % | d,l isomer % |
|---|---|---|---|---|---|
| 1 | Ac—Leu | LeuOBn | HONB | 93 | 0.3 |
| 2 | Ac—Leu | LeuOBn | HOPO | 94 | 0.1 |
| 3[d] | Ac—Leu | LeuOBn | HOBT | 96 | 0.7 |
| 4 | Ac—Leu | ValOBn | HONB | 85 | <0.1 |
| 5 | Ac—Leu | ValOBn | HOPO | 90 | 0.3 |
| 6 | Ac—Leu | PheOBn | HONB | 89 | 0.2 |
| 7 | Ac—Leu | PheOBn | HOPO | 88 | 0.2 |
| 8 | Ac—Val | LeuOBn | HONB | 91 | 0.3 |
| 9 | Ac—Val | LeuOBn | HOPO | 80 | 0.2 |
| 10[d] | Ac—Val | LeuOBn | HOBT | 95 | 1.7 |
| 11 | Ac—Val | ValOBn | HONB | 68 | 0.1 |
| 12 | Ac—Val | ValOBn | HOPO | 85 | 0.1 |
| 13 | Ac—Val | PheOBn | HONB | 86 | 0.2 |
| 14 | Ac—Val | PheOBn | HOPO | 99 | 0.3 |
| 15 | Ac—Phe | LeuOBn | HONB | 83 | 0.4 |
| 16 | Ac—Phe | LeuOBn | HOPO | 95 | 0.5 |
| 17 | Ac—Phe | ValOBn | HONB | 76 | 0.4 |
| 18 | Ac—Phe | ValOBn | HOPO | 90 | 0.5 |
| 19 | Ac—Phe | PheOBN | HONB | 68 | 0.5 |
| 20 | Ac—Phe | PheOBn | HOPO | 65 | 0.5 |
| 21 | Z—Phg | ValOBn | HOPO | 90 | 0.2 |
| 22 | Z—Phg | LeuOBn | HOPO | 92 | 0.2 |
| 23 | Z—Phg | PheOBn | HOPO | 90 | 0.4 |
| 24 | Z—Phg | ValOBn | HOAT | 70 | 0.6 |
| 25 | Z—Gly—Val | ValOBn | HOPO | 89 | 0.2 |
| 26 | Z—Gly—Val | LeuOBn | HOPO | 91 | 0.2 |

[a] Abbreviations: AA$_1$, AA$_2$ = amino acid or dipeptide fragment; Ac = acetyl; Z = (benzyloxy)carbonyl; OBn = benzyloxy.
[b] Reactions (0.2 mmol scale) were carried out in 4 mL of 1:1 i-PrOAc/water (v/v) with 1 eq. of the additive using 1.1 eq. of EDC, at 0–5° C. for 24–40 hrs. then assayed by HPLC, see experimental.
[c] Solution of the amino acid benzyl ester solution in i-PrOAc.
[d] One eq. of HOBT was added, resulting in a suspension in the solvent mixture.

TABLE III

Coupling Reactions in DMF[a,b]

| entry | AA$_1$ | AA$_2$[c] | yield % | d,l isomer % |
|---|---|---|---|---|
| 1 | Ac—Leu | LeuOBn | 99 | 0.4 |
| 2 | Ac—Leu | ValOBn | 97 | 0.4 |
| 3 | Ac—Leu | PheOBn | 97 | 0.7 |
| 4[d] | Ac—Val | LeuOBn | 70 | 21 |
| 5 | Ac—Val | LeuOBn | 94 | 4.6 |
| 6 | Ac—Val | ValOBn | 85 | 3.5 |
| 7[e] | Ac—Val | ValOBn | 93 | 1.0 |
| 8[d] | Ac—Val | ValOBn | 73 | 13 |
| 9 | Ac—Phe | LeuOBn | 99 | 0.5 |
| 10 | Ac—Phe | ValOBn | 99 | 0.5 |
| 11 | Ac—Phe | PheOBn | 96 | 0.4 |
| 12 | Z—Phg | ValOBn | 95 | 4.7 |
| 13 | Z—Phg | LeuOBn | 99 | 4.1 |
| 14 | Z—Phg | PheOBn | 90 | 5.0 |
| 15 | Z—Gly—Val | ValOBn | 94 | 1.8 |
| 16 | Z—Gly—Val | LeuOBn | 96 | 1.6 |

[a] Abbreviations: AA$_1$, AA$_2$ = amino acid or dipeptide fragment; Ac = acetyl; Z = (benzyloxy)carbonyl; OBn = benzyloxy.
[b] One eq. of HOBT was used as the additive unless specified. Reactions (0.2 mmol scale) were carried out in 2 mL of DMF using 1 eq. of EDC, at 0–5° C. for 24–40 hrs. then assayed by HPLC.
[c] The tosylate salts were used with addition of 1 eq. of N-methylmorpholine.
[d] One eq. of HONB was used as the additive.
[e] One eq. of HOPO was used as the additive.

EXAMPLE 2

Preparation of a Tripeptide by Two-Phase Coupling Reaction

Z—Gly—Val

Val—OBn $\xrightarrow{\text{EDC, HOPO}}{\text{iPrOAC/H}_2\text{O}}$

Z—Gly—Val—ValOBn

Procedure: L-Valine benzyl ester tosylate salt (Sigma, 0.76 g, 2.0 mmol) was dissolved in a mixture of 20 mL isopropyl acetate and 20 mL of 1M sodium carbonate. The layers were separated in a 60 mL separatory funnel and the organic layer was washed with 15 mL of saturated aqueous sodium chloride twice. The isopropyl acetate solution was then transferred to a 100 mL round bottomed flask, water (19 mL) was added, followed by N-carbobenzoxy glycyl valine (Sigma, 0.616 g, 2.0 mmol), and 2-hydroxypyridine N-oxide (Aldrich, 20% in water, 1 mL, 2.0 mmol). The mixture was cooled in an ice bath to 0°–5° C. N-Ethyl-N'-[3-(dimethylamino)propyl]carbodiimide hydrochloride (Bachem, 0.422 g, 2.2 mmol) was added slowly. The resulting mixture was stirred at 0°–5° C. for 40 hr. Aqueous hydrochloric acid (2N, 2 mL) was added to quench the reaction. The mixture was transferred to a 60 mL separatory funnel and the layers separated. The organic layer was further washed sequentially with 0.2N hydrochloric acid (10 mL), saturated aqueous sodium chloride (10 mL), 1M sodium bicarbonate (2×10 mL), and sodium chloride (2×10 mL). The isopropyl acetate solution was then dried over sodium sulfate, and filtered. The solvent was evaporated and an oil was obtained (0.973 g, 98% yield), which solidified upon standing.

EXAMPLE 3

Preparation of 1-((7,7-Dimethyl-2-endo-(2S-amino-4-(methylsulfonyl)butyramido)-bicyclo(2.2.1)heptan-1-yl)methanesulfonyl)-4-(2-methylphenyl)-piperazine, Compound A

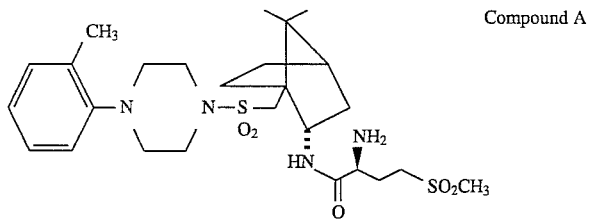

Step A: 1-((7,7-Dimethyl-2-oxo-bicyclo(2.2.1)heptan-1-yl)methanesulfonyl)-4-(2-methylphenyl)piperazine

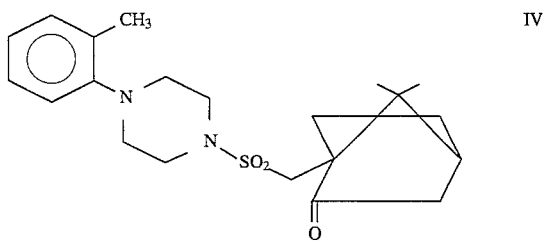

SCHOTTEN-BAUMAN PROCEDURE

To a mechanically stirred suspension of 1-(2-tolyl)piperazine hydrochloride (5.00 kg, 23.5 mol) in toluene (25.0 L) was added 5.0M aqueous sodium hydroxide (11.8 L, 59.1 mol). The mixture was stirred for 0.5 h at 20°–25° C. until all of the solid dissolved. The two-phase mixture was cooled to 0°–5° C. A solution of (+)-10-camphorsulfonyl chloride (7.71 kg, 30.8 mol) in dry toluene (14.0 L) was then added to the rapidly stirred mixture over a 1 h period. During the addition, the reaction temperature was maintained at 0°–5° C. The reaction mixture was stirred for an additional 0.5 h at 0°–10° C., then assayed for completion by HPLC.

| Assay Procedure: | An aliquot (20 μL) of the upper (toluene) layer is diluted to 10.0 mL with 50:50 H$_2$O/MeCN and then analyzed by HPLC. | |
|---|---|---|
| Instrument: | HP 1090M | |
| Column: | 4.6 × 250 mm Inertsil ODS(2) [MetaChem Inc.] | |
| Eluent A: | H$_2$O (0.02M phosphate adjusted to pH 6.0) | |
| Eluent B: | MeCN | |
| Linear Gradient: | 70:30 to 20:80 A:B over 25 minutes | |
| Flow Rate: | 1.5 μL/min. | |
| Temperature: | 45° C. | |
| Injection: | 10.0 mL | |
| Detection: | UV 210 nm | |
| Retention Times: | 1-(2-tolyl)piperazine | 3.03 min. |
| | toluene | 15.3 min. |
| | Ketone Product IV | 20.9 min. |

The reaction was considered complete when less than 1% of 1-(2-tolyl)piperazine (vs the ketone product) remained. If necessary, additional camphorsulfonyl chloride (and aqueous sodium hydroxide depending on the pH of the aqueous layer) can be added.

After the reaction was complete the mixture was warmed to 20°–25° C., and the layers partitioned. The upper (toluene) layer was sequentially washed with 1M aqueous sodium bicarbonate (2×6.4 L) and water (2×6.4 L). The toluene solution was filtered through a medium-porosity sintered glass funnel and then concentrated in vacuo (1000 to 10 mBar, 45° C.) to a volume of ca. 13 L. Heptane (38.5 L) was added slowly while maintaining the temperature at 45° C. The mixture was cooled to 20°–25° C., aged for 15 h at this temperature, filtered, and the cake washed with 9:1 (v/v) heptane/toluene (2×2.5 L) and heptane (2×2.5 L). The product was air-dried, and then dried in vacuo (100 mBar, nitrogen sweep, 45° C.) to constant weight to afford ketone IV as an off-white Crystalline solid.

mp: 124°–127° C.
HPLC: >99 area % (above method)
$^1$HNMR: consistent
Specific Rotation: [a]589=+22.8° (c=1.02 MeOH)

Step B: 1-((7,7-Dimethyl-2-oximino-bicyclo(2.2.1)heptan-1-yl)methanesulfonyl)-4-(2-methylphenyl)-piperazine

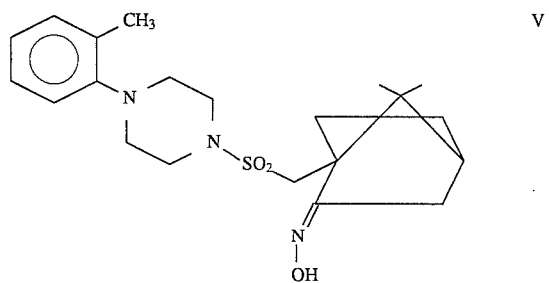

SODIUM ACETATE PROCEDURE

A mechanically stirred suspension of the ketone IV (from Step A above) (4.40 kg, 11.3 mol), hydroxylamine hydrochloride (1.18 kg, 16.9 mol) and sodium acetate (1.20 kg, 14.7 mol) in ethanol (22 L) was heated for 34 h at reflux to give the corresponding oxime product. The progress of the reaction can be followed by HPLC.

Assay Procedure: An aliquot (100 μL) is diluted to 25.0 mL with 50:50 H$_2$O/MeCN and then analyzed by the previously described HPLC method.

| Retention Times: | (oxime V) | 19.2 min. |
|---|---|---|
| | (ketone IV) | 20.9 min. |

The reaction was considered complete when less than 1% of the ketone remained unreacted. After the reaction was complete, the mixture was cooled to 60°–65° C. At this point water (44 L) was added over a 0.5 h period. The mixture was stirred for 14 h at 20°–25° C., cooled to 10° C., and then stirred at this temperature for 4 h. The mixture was filtered and the cake washed with water (3×4.0 L). The resultant product was air-dried, and then dried in vacuo (100 mBar, nitrogen sweep, 45° C.) to constant weight to afford the oxime V as a white crystalline solid.

mp: 170°–172° C.
HPLC: 99 Area % (Above Method)
Specific Rotation: [a]589=−8.17° (c=1.0 MeOH)
$^1$H NMR: consistent Step C: Preparation of Corresponding Endo Amine

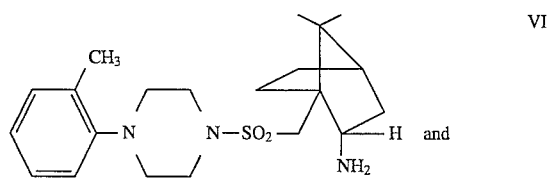

and

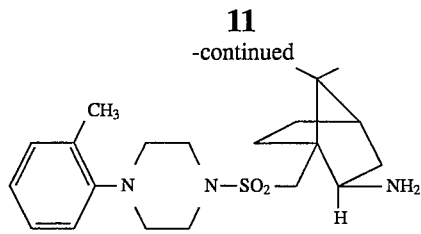

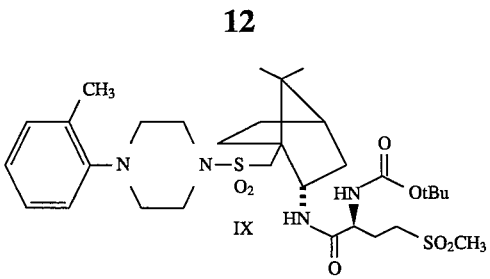

ENDO SELECTIVE COUPLING REACTION

RANEY NICKEL IN METHANOL PROCEDURE

A suspension of oxime of Step B (900 g, 2.22 mol), 5.0N aqueous sodium hydroxide (0.445 L, 2.22 mol), and Raney nickel (500 g) in methanol (12 L) was pumped into a 20-L Hastelloy autoclave, followed by a rinse of methanol (1.5 L). The vessel was purged with nitrogen, and then pressurized to 3 atm (44 psi) with hydrogen. (Caution: the vessel must be purged with nitrogen prior to the introduction of hydrogen.) The reaction mixture was vigorously agitated at 25°–30° C. while monitoring the progress of the reaction by hydrogen uptake and/or HPLC.

Assay Procedure: An aliquot (500 mL) is diluted to 25.0 mL with 50:50 (v/v) $H_2O$ (0.02M $KH_2PO_4$)/MeCN and then analyzed by the previously described HPLC method.

Retention Times:

Endo amine VI 12.0 min.

Exo amine VII 17.1 min.

Oxime V 19.2 min.

After 16 h, the reaction was found to be 95% complete (5% unreacted oxime) with an endo/exo ratio of 87:13. The vessel was charged with additional Raney nickel (200 g), and the mixture vigorously agitated for 6 h at 25°–30° C. At this point the reaction was considered to be complete (<0.3% untreated oxime) with an endo/exo ratio of 87:13.

The batch was transferred out of the autoclave, and the autoclave rinsed with methanol (4 L). The mixture was filtered through a medium frit sintered-glass funnel containing a small bed of "Celite®" (ca. 1 in, previously washed with 0.1M sodium hydroxide in methanol). The catalyst cake was washed with the autoclave rinse (divided into three portions) and finally with fresh methanol (2.5 L). [Caution: Raney nickel is easily ignited when dry. Great care must be taken during this filtration and subsequent handling. The catalyst must never be sucked dry in the presence of oxygen (air) and should always be covered with the solvent in use, and finally with water after all of the product has been washed from the catalyst cake. A nitrogen filled plastic bag was used to cover the filter pot during this operation.] The filtrate and cake washes were combined and then concentrated in vacuo (1000 to 100 mBar, 20°–30° C.) to a volume of 4 L. During the concentration the product began to crystallize to give a thick (but stirrable) slurry. The mixture was diluted with water (16 L), and the concentration continued to a volume of 16 L. The mixture was then stirred for 24 h at 20°–25° C., was filtered, and the product washed with water (4×1 L; until the pH of the wash was neutral). The product was air-dried, and then dried in vacuo (100 mBar, 40°, nitrogen sweep) to constant weight to give the amine product as a white crystalline solid.

mp: 145°–147° C.

HPLC: 87:13 endo/exo ratio (Above Method)

$^1$ H NMR: consistent

Step D: 1-((7,7-Dimethyl-2-endo-(2S-(tert-butyloxycarbonylamino)-4-(methyl-sulfonyl)-butyramido)-bicyclo(2.2.1)-heptan-1-yl)methanesulfonyl)-4-(2-methylphenyl)piperazine In a 100-L reaction vessel fitted with a mechanical stirrer, teflon-coated cooling coils, teflon-coated thermocouple probe, and nitrogen inlet containing a solution of the amine VI+VII (3.60 kg total; 87:13 endo/exo; 3.13 kg, 8.00 mol endo) in isopropyl acetate (53 L) were sequentially added water (21 L), N-BOC-(S)-methionine sulfone (2.36 kg, 8.40 mol), and hydroxybenzotriazole hydrate (HOBT, 61 g, 0.40 mol). The mixture was stirred at 20°–25° C. until all solids dissolved, and was then cooled to 0°–2° C. To the rapidly agitated mixture was added ethyl-3-(3-dimethylamino)propyl carbodiimide hydrochloride (EDC, 1.69 kg, 8.80 mol) portionwise over a 0.5 h period, while maintaining the internal temperature at 0°–2° C. The mixture becomes two clear phases after the addition of EDC. The mixture is stirred for 18 h at 0°–2° C. The progress of the reaction can be followed by HPLC.

Assay Procedure: An aliquot (250 μL) is diluted to 50.0 mL with 50:50 (v/v) $H_2O$ (0.02M $KH_2PO_4$)/MeCN and then analyzed by the previously described HPLC method.

| Retention Times: | | |
|---|---|---|
| N-BOC-(S)-methionine sulfone | 1.9 min. |
| HOBT | 2.6/2.8 min |
| Endo Amine VI | 12.0 min. |
| Exo Amine VII | 17.1 min. |
| Exo isomer of N-BOC-Protected Amine | 20.5 min |
| Endo isomer of N-BOC-Protected Amine IX | 21.4 min |

The reaction is considered complete when the amount of endo amine VI remaining unreacted in <2%, with the endo/exo ratio of the product 98:2. Increasing the amount of EDC or N-BOC-(S)-methionine Sulfone used results in more of the exo amine VII reacting, thereby decreasing the selectivity of the coupling reaction. After the reaction was complete, 2N aqueous hydrochloric acid (7.0 L) was added, and the mixture was warmed up to 16° and stirred for 15 min at 20° C. The mixture was allowed to settle, and the bottom (aqueous) layer was removed. The upper (product) layer was sequentially washed with water (10 L), 1M aqueous sodium bicarbonate (10 L), and finally water (10 L). The solution was then concentrated in vacuo (1000 to 100 mBar, 35°–40° C.) to a volume of 10 L. The solution was diluted with n-propanol (30 L) and was then concentrated in vacuo (100 mBar, 40°–45° C.) to a volume of 10 L to remove the remaining isopropyl acetate. The solution was diluted with n-propanol to a volume of 21 L, heated to 45°–50° C., and then diluted with water (10.5 L). The product was then crystallized by allowing the mixture to slowly cool to 20° C. (seeding if necessary). The mixture was stirred for 48 h at 20°–22° C., was filtered, and the cake washed with 60:40 (v/v) n-propanol/water (2×5 L). The product was air-dried, then dried in vacuo (10 mBar, 45° C.) to constant weight.

Yield: 4.72 kg (90% yield) of N-BOC Protected Amine IX as a white crystalline solid.

mp: 101°–103° C.

HPLC: >99.9% endo/exo (above HPLC method)

$^1$H NMR: consistent

Specific Rotation: [a]1589=+3.1° (c 1.0, MeOH)

Step E: Preparation of Crude Free Base I via Trifluoroacetic Acid Deprotection Procedure

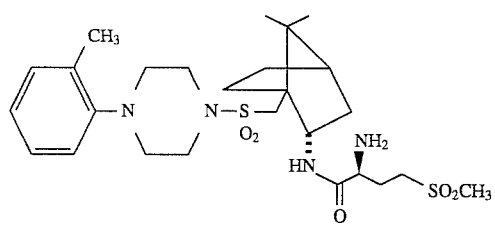

To a mechanically stirred solution of N-BOC protected amine IX (90 g, 140 mmol) in toluene (900 mL) at 20° C. was added trifluoroacetic acid (TFA, 160 g, 1.40 mol) portionwise over a 0.5 h period. During the initial stages of the addition the internal temperature rose to ca. 30° C. The mixture was stirred for 18–24 h at 20°–25° C. During the course of the reaction, a second liquid phase (containing the trifluoroacetic acid salt of amine I) is formed. The progress of the reaction can be monitored by HPLC.

Assay Procedure: An aliquot (250 μL) of the toluene layer is diluted with ethanol (5 mL), is concentrated in vacuo (to remove the majority of the toluene), the residue is diluted to 50.0 mL with (50:50 v/v) H$_2$O (0.02M KH$_2$PO$_4$)/MeCN, and is then analyzed by the previously described HPLC method. In addition, an aliquot (25 μL) of the TFA layer, is worked-up and analyzed by the same procedure.

| Retention Times: | Amine I | 14.8 min. |
|---|---|---|
| | Toluene | 15.3 min. |
| | exo Isomer of N-BOC-Protected Amine | 20.5 min. |
| | endo Isomer of N-BOC-Protected Amine IX | 21.4 min. |

The reaction is considered complete when the amount of N-BOC Protected Amine IX remaining is <2%. After the reaction was complete, the mixture was cooled to 5° C. To the well stirred mixture was then added water (620 mL), while maintaining the internal temperature <10° C. The vessel was fitted with a pH probe. To the well stirred mixture was then added 5M aqueous sodium hydroxide (282 mL, 1.41 mol) portionwise while monitoring the pH of the aqueous phase. The internal temperature rose to 20°–25° C. during the addition. The pH rose to 12 by the end of the addition. After the neutralization was complete, agitation was stopped, and the mixture was partitioned. The upper (toluene) layer was washed with water (2×90 mL) to remove residual sodium hydroxide and/or sodium trifluoroacetate. The toluene layer was then extracted with 1M aqueous hydrochloric acid (2×700 mL). The two aqueous extracts were combined and then washed toluene (1×700 mL) to remove any residual N-BOC Protected Amine IX. The aqueous layer, containing the amine I, was adjusted to pH 10 with 5M aqueous sodium hydroxide (282 mL, 1.41 mol) and the product then extracted into toluene (800 mL). The toluene layer was washed with water (2×80 mL) to remove residual sodium hydroxide and/or sodium chloride. The toluene layer was then concentrated in vacuo (1000 to 100 mBar, 40°–45° C.) to a syrup, and was then flushed with methanol (3×250 mL) to displace the residual toluene. The residue was then dissolved in methanol, bringing the volume to 700 mL. This solution containing the crude amine I as the free base can be carded on "as is" to form a pharmaceutically acceptable salt by standard methods know to those of ordinary skill in the art.

HPLC: 99.8:0.2 endo/exo

EXAMPLE 4

Preparation of [3(R)-(–)-[2-(Pyridin-4-yl)ethyl]-2-piperidon-1-yl]acetyl-3(R)-methyl-β-alanine, Compound B

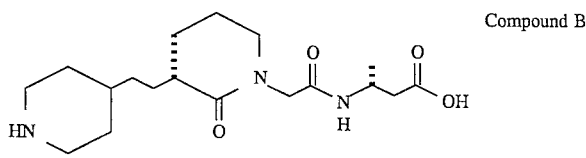

Step A: Preparation of Ethyl (2-Piperidon-1-yl)acetate (5) N-alkylation

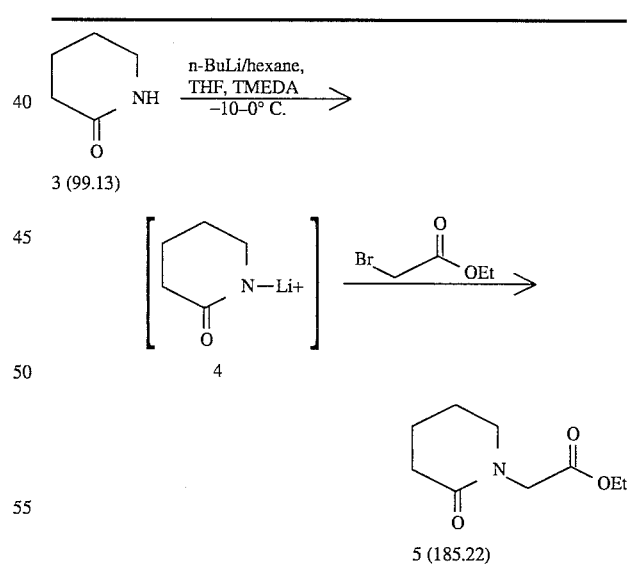

| materials | amount | mole | equivalent |
|---|---|---|---|
| 2-Piperidone (3) (FW = 99.13) (KF < 2 mol %) (BASF) | 160.00 g | 1.614 mol | 1.0 equiv |
| Tetrahydrofuran (THF) (KF ≦ 10 μg/mL) | 1.92 L | | |
| Tetramethylethylenediamine (TMEDA) | 206.30 g (268 mL) | 1.775 mol | 1.1 equiv |

15
-continued

| | | | |
|---|---|---|---|
| (FW = 116.21) | | | |
| (d = 0.77) | | | |
| (KF ≦ 30 µg/mL) | | | |
| n-Butyllithium (1.6M in hexane) | 1.06 L | 1.695 mol | 1.05 equiv |
| Ethyl bromoacetate | 283.10 g | 1.695 mol | 1.05 equiv |
| (FW = 167.01) | (188 mL) | | |
| (d = 1.506) | | | |
| (Aldrich, 98%) | | | |
| Hydrochloric acid (2M) (FW = 36.46) | 1.78 L | 3.55 mol | 2.2 equiv |
| Sodium chloride | 170 g | | |
| Isopropyl acetate | 3 L | | |
| Acetonitrile | 2.3 L | | |
| (KF < 30 µg/mL) | | | |

A 5 L four-necked round bottom flask was charged with 2-piperidone 3 (160.00 g, 1.614 mol), THF (1.44 L) and TMEDA (206.3 g, 1,775 mol). The mixture was stirred until all the solid dissolved, then 3 Å molecular sieves (26 g) were added. After stirring overnight, the mixture was filtered and the molecular sieves were washed with THF (0.48 L).

The combined filtrate was transferred to a dry 5 L four-necked round bottom flask equipped with a mechanical stirrer, an addition funnel, nitrogen inlet, cooling unit and a thermometer probe. The solution was cooled to −10° C. and n-butyllithium (1.6M in hexane, 1.06 L, 1.695 mol) was slowly added over a 60 min period, keeping the internal temperature less than 0° C.

After the addition, the reaction mixture was stirred at 0°–5° C. for 1 h. The reaction mixture was cooled to −10° C., and ethyl bromoacetate (283.1 g, 1.695 mol) was added over 15 min while maintaining the internal temperature less than 0° C. The reaction mixture was stirred at 0° C. for 15 min and then allowed to warm to 23° C. and aged at this temperature for a 2 h period (or overnight if needed).

The reaction mixture was cooled to −5°–0° C. and quenched into a solution of NaCl (170 g) in 2N HCl (1.78 L), keeping the internal temperature less than 20° C. The resulting aqueous phase should be at pH 6. The mixture was transferred to a 12 L separatory funnel and the two layers were separated. The aqueous layer was extracted with i-propyl acetate (3×1 L).

The combined organic layers were concentrated to near dryness and then azeotropically dried with acetonitrile (3×600 mL) (50° C., house vacuum). The mixture was filtered to remove a small amount of NaCl after the azeotropic distillation. The filter cake was washed with 500 mL acetonitrile. The combined filtrate contained the product and the brown solution was used "as is" in the next step.

| HPLC conditions: | |
|---|---|
| Column: | 4.6 mm × 25 cm Zorbax RX-C8 |
| Eluent A: | MeCN |
| Eluent B: | H₂O—Na₂HPO₄/NaH₂PO₄ buffer pH 6.0, 10 mM |
| Isocratic: | 50:50 |
| Flow rate: | 1.50 mL/min |
| Detection: | 215 nm |
| Temperature: | 22° C. |
| Retention Times: | 2 piperidone 1.90 min |
| | product 2.25 min |
| | ethyl bromoacetate 3.90 min |

Pure solid product can be isolated by recrystallization from IPAC/Hexanes.

mp: 70°–71° C.

$^1$HNMR (CDCl$_3$, 250 MHz) δ: 1.27 (t, J=7.1 Hz, 3H), 1.85 (br m, 4H), 2.42 (br m, 2H), 3.35 (br m, 2H), 4.10 (s, 2H), 4.19 (q, J=7.1 Hz, 2H).

$^{13}$CNMR (CDCl$_3$, 63 mHz) δ: 14.1, 21.3, 23.1, 32.1, 48.6, 49.2, 61.1, 169.1, 170.4.

Step B: Preparation of Ethyl [(+)3-[2-(Pyridin-4-yl)ethyl]-2-piperidon-1-yl]acetate (7)

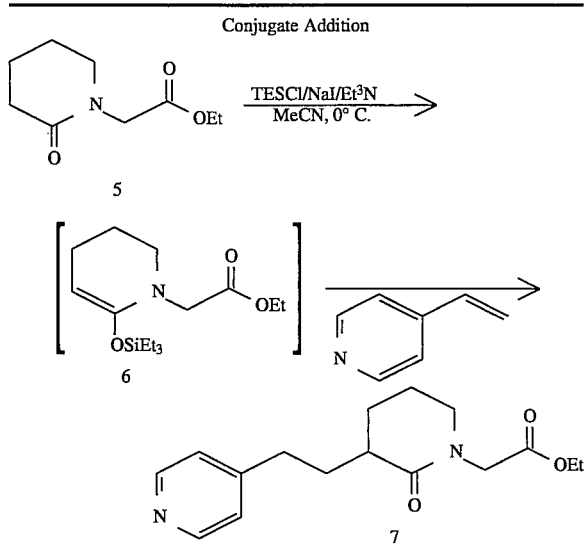

| materials | amount | mole | equivalent |
|---|---|---|---|
| Ethyl (2-Piperidon-1-yl)acetate (5) 36 wt % in MeCN (FW = 185.22) (KF < 160 µg/mL) | 20.0 g (55.6 g of solution) | 108.0 mmol | 1.0 equiv |
| Acetonitrile (d 0.786) (KF ≦ 35 µg/mL) | 63 mL | | |
| Triethylamine (FW = 101.2) (d = 0.726) (KF ≦ 30 µg/mL) | 13.11 g (18.1 mL) | 129.6 mmol | 1.2 equiv |
| Sodium Iodide, anhydrous (FW = 149.9) (KF ≦ 650 µg/ g = 0.5 mol %) | 17.81 g | 118.8 mmol | 1.1 equiv |
| Chlorotriethylsilane, 98% (TES-Cl) (FW = 150.73) (d = 0.898) | 17.91 g (20.0 mL) | 118.8 mmol | 1.1 equiv |
| 4-Vinylpyridine, 95% (FW = 105.4) (d = 0.975) (KF ≦ 30 µg/mL) | 13.1 g (13.43 mL) | 124.2 mmol | 1.15 equiv |
| Hydrochloric acid (1N) (FW = 36.46) | 140 mL | 140 mmol | 1.3 equiv |
| Hexanes | 160 mL | | |
| Isopropyl Acetate | 295 mL | | |
| Sodium Hydroxide (5N) | 22 mL | | |
| Sodium Bicarbonate (NaHCO₃) | 10 g | | |
| Saturated Aq. NaHCO₃ | 150 mL | | |
| Toluene | 670 mL | | |
| Silica Gel, 60–200 mesh | 12 g | | |
| Isopropyl alcohol, anhydrous | 675 mL | | |

A 250 mL three-necked round bottom flask equipped with a stirrer, nitrogen inlet, cooling unit and a thermometer probe was charged with piperidone-ester 5 (55.6 g, 108.0 mmol; 36 wt %; from step A), acetonitrile (63.0 mL), anhydrous sodium iodide (17.81 g, 118.8 mmol) and triethylamine (13.11 g, 129.6 mmol). The mixture was stirred until all the solid dissolved.

The solution was cooled to 0° C. and chlorotriethylsilane (17.91 g, 19.94 mmol) was added over 5 min, keeping the internal temperature below +5° C., and then stirred at 20° C. for 1–2 h.

The resulting mixture was cooled to −5°–0° C., and 4-vinylpyridine (13.09 g, 124.2 mmol) was added dropwise over a 2 h period, while keeping the internal temperature below 0° C. The reaction was aged at 0° C. for 1–2 h, then quenched by slow addition into a cold (0° C.) solution of 1N HCl (140 mL), while keeping the internal temperature <20° C. The final pH should be 1.5–2.5.

The acidic solution (pH~2) was extracted with 50% IPAC/Hexane (2×160 mL). The aqueous layer was assayed by the following process which indicated the presence of product 7.

HPLC assay:

Column: Zorbax RX-C8 4.6 mm×25 cm column

Temperature: Ambient

Detection: 220 nm

Flow rate: 1.5 ml/min

Eluent: 50% acetonitrile and 50% 20 mM $NaH_2PO_4$/$Na_2HPO_4$ pH 6.0 buffer.

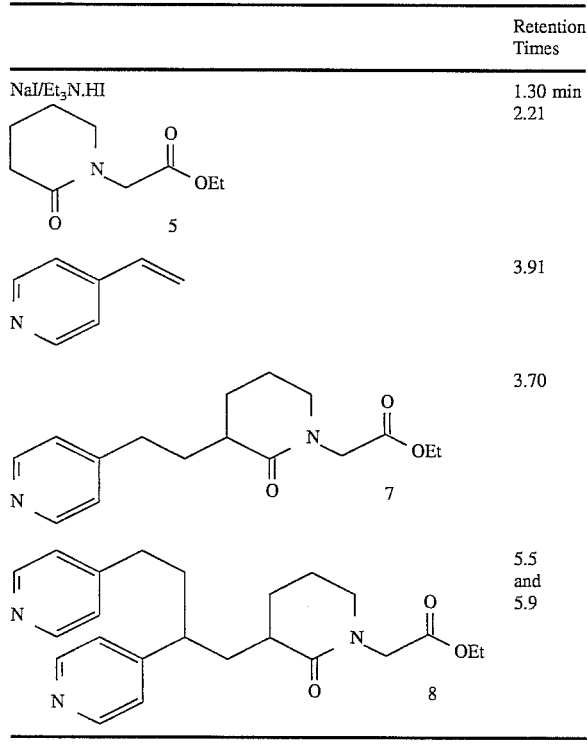

| | Retention Times |
|---|---|
| NaI/Et₃N.HI | 1.30 min 2.21 |
| (compound 5) | |
| (4-vinylpyridine) | 3.91 |
| (compound 7) | 3.70 |
| (compound 8) | 5.5 and 5.9 |

To the aqueous solution was added IPAC (1×120 mL) and the mixture was cooled to 5°–10° C. With vigorous stirring, it was then basified to pH 9.5–10 by the slow addition of solid sodium bicarbonate (10 g; to pH 6) and 5N NaOH (~22 mL; to pH 9.7). The layers were separated.

The aqueous was extracted with toluene (2×150 mL). The combined organic layers were washed with saturated aqueous sodium bicarbonate (3×50 mL).

The organic layer was azeotropically dried by distillation at 60° C. under reduced pressure. After 450 mL distilled out (final KF=<100 μg/mL), distillation was terminated and 150 mL dry toluene (total volume=200 mL) and 12 g of silica (60–200 mesh) were added. After stirring for 1 h, the mixture was filtered and the filter cake was washed with 100 mL toluene.

The combined filtrate was assayed to contain product 7. It was concentrated in vacuo (50° C., 100 mBar). After distilling most of the solvent, the batch was flushed with IPA (3×100 mL) to give a final concentration of 25 wt % (86 g) in IPA. This solution was used as is in the next step.

MS(EI) m/z 290 (M⁺).

¹H NMR (CDCl₃) δ 1.09 (t, J=7.1 Hz, 3H), 1.50 (m, 1H), 1.60–1.90 (m, 2H), 2.04 (m, 1H), 2.20 (m, 1H), 2.54 (m, 2H), 3.10–3.30 (m, 2H), 3.77(A of AB, J=17.2 Hz, 1H), 4.01 (q, J=7.1 Hz, 2H), 4.03 (B of AB, J=17.2 Hz, 1H), 6.99 (d, J=6.0 Hz, 2H), 8.30 (d, K=6.0 Hz, 2H).

¹³C NMR (CDCl₃) δ 9.7, 17.3, 22.2, 27.9, 28.0, 36.2, 44.6, 44.9, 56.6, 119.5, 145.2, 146.6, 164.7, 168.2.

Pure product is an oil (purified by flash chromatography).

Step C: Preparation of [(±)3-[2-(Pyridin-4-yl)ethyl]-2-piperidon-1-yl]acetic acid (9)

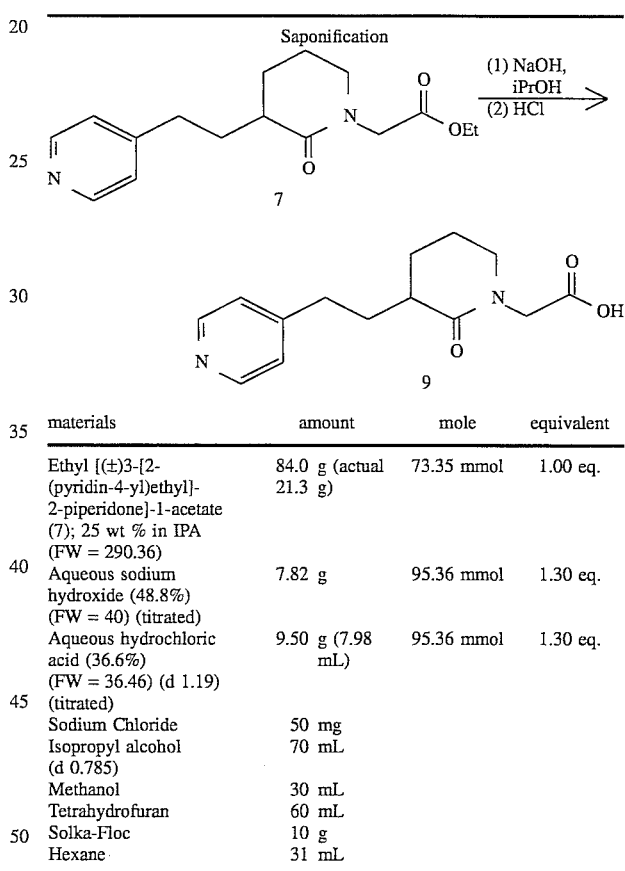

| materials | amount | mole | equivalent |
|---|---|---|---|
| Ethyl [(±)3-[2-(pyridin-4-yl)ethyl]-2-piperidone]-1-acetate (7); 25 wt % in IPA (FW = 290.36) | 84.0 g (actual 21.3 g) | 73.35 mmol | 1.00 eq. |
| Aqueous sodium hydroxide (48.8%) (FW = 40) (titrated) | 7.82 g | 95.36 mmol | 1.30 eq. |
| Aqueous hydrochloric acid (36.6%) (FW = 36.46) (d 1.19) (titrated) | 9.50 g (7.98 mL) | 95.36 mmol | 1.30 eq. |
| Sodium Chloride | 50 mg | | |
| Isopropyl alcohol (d 0.785) | 70 mL | | |
| Methanol | 30 mL | | |
| Tetrahydrofuran | 60 mL | | |
| Solka-Floc | 10 g | | |
| Hexane | 31 mL | | |

To a 25 wt % solution of the pyridine-ethyl ester 7 (21.3 g, 73.35 mmol) in isopropyl alcohol was added 48.8% aqueous sodium hydroxide (7.82 g, 95.36 mmol) at 20° C. under nitrogen over a 5 min period.

The reaction mixture was stirred for 2 h until complete consumption of 7 was observed as monitored by HPLC.

The reaction was monitored by following the disappearance of 7 (RT=3.7 min using Zorbax RX-C8 4.6 mm×25 cm column, detection at 220 nm, ambient temperature, flow rate of 1.5 ml/min and elution with 50% acetonitrile and 50% 20 mM $NaH_2PO_4$/$Na_2HPO_4$ pH 6.0 buffer).

The mixture was cooled to 5°–10° C., seeded with 50 mg of NaCl and then quenched by the slow addition of 36.6% aqueous hydrochloric acid (9.50 g, 95.36 mmol) over a 10 min period, while maintaining the internal temperature <15° C. The final pH was 5.45.

To the resulting mixture was added MeOH (20 mL), THF (40 mL) and Solka-Floc (5 g). After stirring for 30 min at ambient temperature, the mixture was filtered through a pad of Solka-Floc (5 g, wetted with 10 mL IPA) in a 150 mL sintered glass funnel (10–15 μm).

The filter cake was washed with a mixture of IPA/THF/MeOH (50 mL:20 mL:10 mL). The combined filtrate contained acid 9 as determined by HPLC analysis.

HPLC conditions are: Zorbax Phenyl 4.6 mm×25 cm column, detection at 220 nm, ambient temperature, flow rate of 1.5 ml/min and elution with 65% acetonitrile and 35% 0.1% $H_3PO_4$ in water. Retention time of 9 is 3.01 min.

The filtrate was dried by azeotropic distillation under vacuum at 50° C. After distilling most of the solvents, the mixture was flushed several times with IPA (3×50 mL) to give a final concentration of 30 wt % (final weight=60 g) and a KF of <1000 μg/mL.

The mixture was seeded with 9 and stirred until a seed bed was formed. Hexane (20 g, 30.5 mL) was then added over a 1 h period and then aged for 12 h. After cooling to 10° C. and stirring for 0.5 h, the solid was collected by filtration through a sintered glass funnel. The filter cake was washed with 40:60 IPA:hexanes (50 mL) and vacuum-dried under a stream of nitrogen to give 9 as a light beige crystalline solid.

mp 144°–145° C.

MS(EI) m/z 263 ($MH^+$).

$^1$H NMR ($CDCl_3$) δ 1.70 (m, 1H), 1.80–2.05 (m, 4H), 2.20 (m, 1H), 2.40 (m, 1H), 2.78 (t, J=8.0 Hz, 2H), 3.35 (m, 1H), 3.47 (m, 1H), 3.90 (A of AB, J=17.1 Hz, 1H), 4.32 (B of AB, J=17.1 Hz, 1H), 7.27 (d, J=6.2 Hz, 2H), 8.49 (d, J=6.0 Hz, 2H).

$^{13}$C NMR ($CDCl_3$) δ 17.4, 22.4, 28.1, 28.4, 36.3, 44.9, 45.1, 120.4, 142.7, 149.8, 167.7, 168.3.

Anal. Calcd for $C_{14}H_{18}O_3N_2$: C, 64.11; H, 6.92;N, 10.68. Found: C, 64.15; H, 7.16;N, 10.66.

Step D: Preparation of Quininium [3(R)-(−)-[2-(Pyridin-4-yl)ethyl]-2-piperidon-1-yl]acetate (12) via Resolution of [(±)3-[2-(Pyridin-4-yl)ethyl]-2-piperidon-1-yl]acetic Acid (9) with Quinine Resolution - Salt Formation and Crystallization

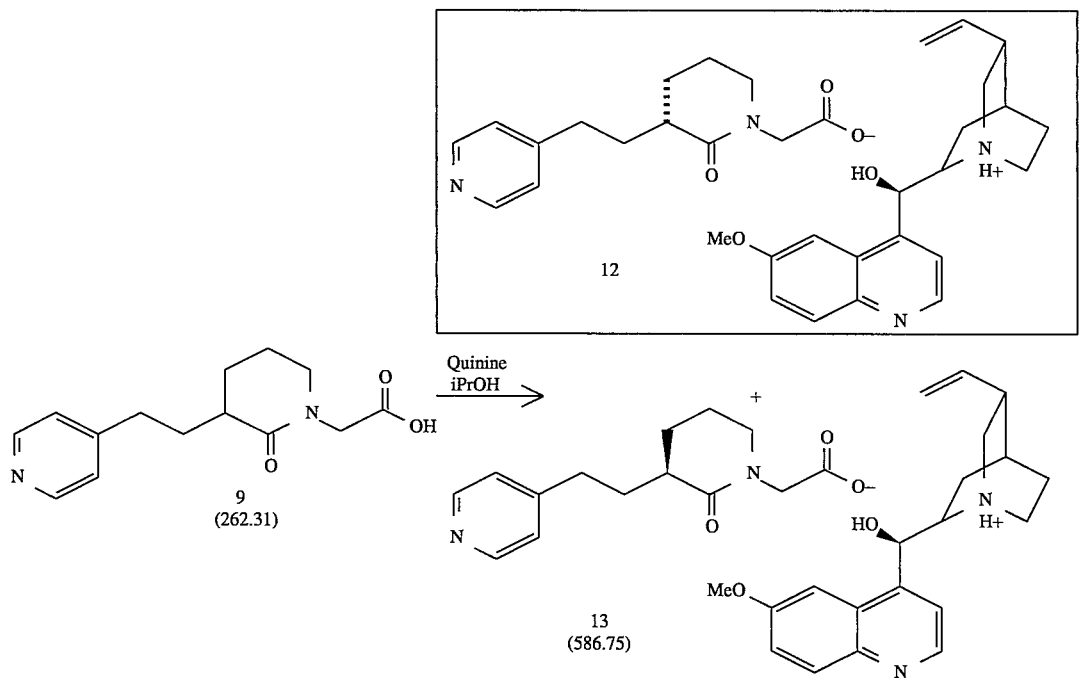

| materials | amount | mole | equivalent |
| --- | --- | --- | --- |
| (±)-[3-[2-(Pyridin-4-yl)-ethyl]-2-piperidon-1-yl]acetic Acid (9) (FW = 262.31) (96.6 wt %) | 12.04 g (actual 11.63 g | 45.90 mmol 44.34 mmol) | |
| Quinine (FW = 324.44) (Aldrich, 90%) | 14.89 g | 45.90 mmol | '1.00 eq' |
| i-Propyl alcohol (KF ≦ 100 μg/mL) | 80.8 mL | | |
| THF (KF ≦ 100 μg/mL) | 40 mL | | |
| Hexane | 40 mL | | |

In a 250 mL round bottom flask, pyridine acid 9 (12.04 g, 96.6% pure, 44.34 mmol), quinine (14.89 g, 45.90 mmol) and isopropyl alcohol (80.8 mL; KF<0.1 mg/mL) were combined. The mixture was heated at 65° C. for 15 min under a nitrogen atmosphere to dissolve all the solid. The resulting solution was allowed to cool to 20° C. When the solution reached 45° C., it was seeded with ~10 mg of 99.5% ee quinine salt 12. After stirring overnight, the mixture was cooled to 5°–6° C. and aged for 0.5–1 h.

The solid was collected on a medium porosity fritted funnel under a nitrogen blanket. The filter cake was washed with 50 mL cold (5°–10° C.) THF:hexane (50:50) and then dried under vacuum with a nitrogen sweep to give 12 as a white solid. The optical purity of the free acid was 98% ee (enantiomeric excess).

TG and NMR studies indicated that the crystalline solid is a mono-IPA solvate.

The chemical purity of 12 was determined by reverse phase HPLC analysis:

| Column: | 4.6 × 250 mm Zorbax Phenyl |
|---|---|
| Eluent: | 40:60 MeCN:0.1%$H_3PO_4$ in water |
| Flow Rate: | 1.5 mL/min |
| Detection: | 220 nm |
| Retention: | pyridine acid 3.3 min |
| | quinine 6.6 min |

The optical purity of the pyridine acid was determined by normal phase HPLC analysis via the chiral amides of (R)-(+)-1-(1-naphthyl)ethylamine. The preparation of the chiral amides and the HPLC conditions are described below.

1. To 12 mg of pyridine acid quinine salt is added 1 mL THF.
2. Add 66 μL of HOBT-$H_2O$/THF solution (1 mg/20 μl).
3. Add 41 μL of (R)-(+)-1-(1-naphthyl)ethylamine/MeCN solution (1 mg/10 μl; MW=171.25).
4. Add 4.6 mg of EDC, and sonicate for 5 min.
5. Dilute to 15 mL (or 20 mL) with $CH_2Cl_2$ (OmniSolv).
6. Wash with water (2×15 mL).
7. Filter $CH_2Cl_2$ layer through pad of anhydrous $MgSO_4$/$SiO_2$.
8. Inject solution on HPLC.

Column: 4.6×250 mm Zorbax Silica

Eluent: 980:17:3 $MeCl_2$/IPA/15M aqueous $NH_4OH$

Flow Rate: 1.0 mL/min

Injection: 20 μL

Detection: 260 nm

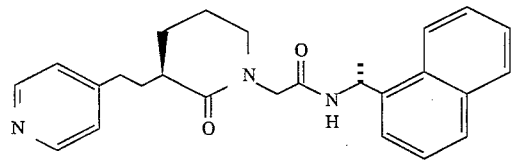

(S,R)-Diastereomer (minor, RT 7.3 min)

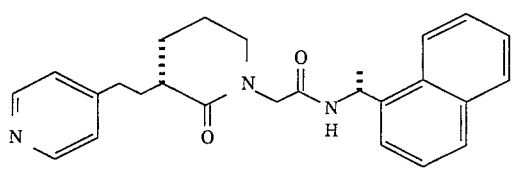

(R,R)-Diastereomer (major, RT 7.9 min)

If the optical purity of 12 is less than 96% ee, the material is recrystallized one more time using the same procedure as described above. This will usually give 99+% ee material.

Step E: Preparation of [3(R)-(−)-[2-(Pyridin-4-yl)ethyl]-2-piperidon-1-yl]acetyl-3-(R)-methyl-β-alanine benzyl ester (15)

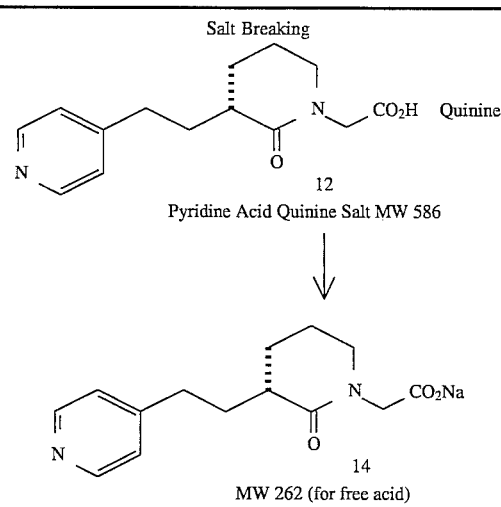

| Materials | |
|---|---|
| Pyridine Acid | 10 g, MW 587, 15 mmol |
| Quinine Salt (89.5 wt %) | (1.98 g pyridine acid, MW |
| (39.7% wt Pyridine Acid, | 262, 15 mmol) |
| 97.6% ee) | |
| Methyl t-Buty Ether (MTBE) | 185 mL |
| 2N Sodium Hydroxide | 7.5 mL |

To a three-necked flask charged with 140 mL MTBE and 7.5 mL water was added 10 g of pyridine acid quinine salt 12. To this stirred suspension was added 7.5 mL 2N sodium hydroxide slowly. The final pH of the aqueous solution should be controlled to <12. After separation of two layers, the aqueous layer was extracted with 45 mL MTBE.

HPLC Assay: same as before.

The recovery of the pyridine acid was quantitative by HPLC.

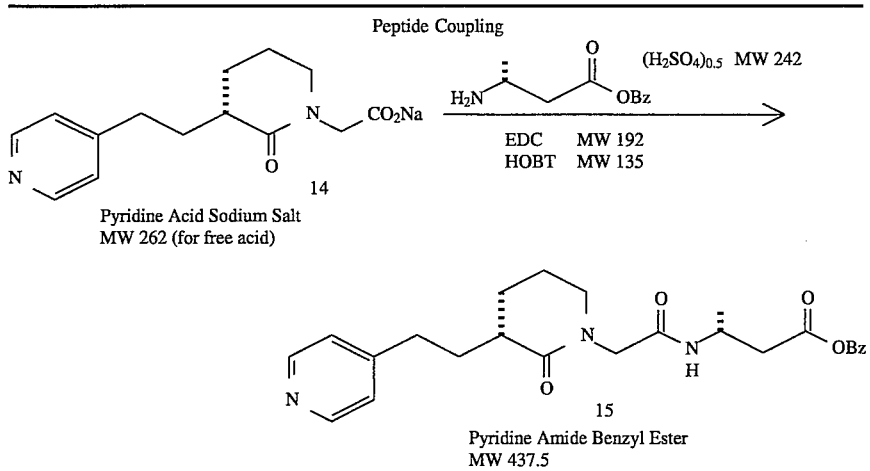

| Materials | | |
|---|---|---|
| Pyridine Acid Sodium Salt Solution | | 14 mmol |
| Benzyl 3(R)-Aminobutyrate Hemisulfate | 3.48 g MW 242.3 | 14.36 mmol |
| Isopropyl Acetate | 59 mL | |
| 1-Hydroxybenzotriazole hydrate (HOBT) | 0.14 g MW 135 | 1 mmol |
| 1-(3-Dimethylaminopropyl)-3-ethyl carbodiimide hydrochloride (EDC) | 3.29 g MW 191.7 | 17.16 mol |
| 5% Sodium Bicarbonate Solution | 15 mL | |
| Water | 60 mL | |
| 1N HCl | ~0.4 mL | |

The pH of the aqueous solution of pyridine acid sodium salt 14 (14 mmol) from the last step was adjusted with 1N HCl if necessary to 9–11.5. To this stirred solution of pyridine acid sodium salt was added benzyl 3(R) aminobutyrate hemisulfate (3.48 g, 14.36 mmol), isopropyl acetate (59 mL), HOBT (0.14 g, 1 mmol) and EDC (3.29 g, 17.16 mmol). The mixture was stirred at room temperature for 2–3 hrs until all the pyridine acid was consumed as judged by HPLC.

The reaction mixture was cloudy (two layers) but all the solids were dissolved.

HPLC assay: Same as before.

After the reaction was complete, the two layers were separated. The aqueous layer was extracted with another 14.7 mL isopropyl acetate. The combined organic layers were washed with 15 mL 5% sodium bicarbonate solution and then with 2×30 mL water. The combined organic solution was used directly for the next reaction.

Step F: Preparation of [3(R)-(−)-[2-(Pyridin-4-yl)ethyl]-2-piperidon-1-yl]acetyl-3-(R)-methyl-β-alanine (Compound B)

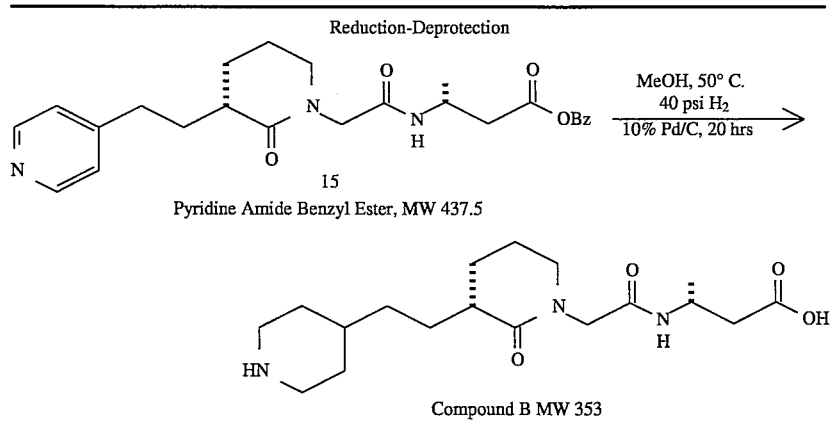

| Materials | Amount | Mole |
|---|---|---|
| Pyridine Amide Benzyl Ester (Solution in Methanol) | 4462 g, MW 437.5 | 10.2 mol |
| Acetic Acid | 55 ml | 0.97 mol |

| | |
|---|---|
| Methanol (EM OmniSolv, KF < 300 mcg/ml) | 22.3 L |
| 10% Palladium on Charcoal | 446 g |
| Solka Floc (Dried in vacuum oven at 60° C. over night) | 1 kg |
| Acetonitrile (KF < 200 μg/ml) | 56 L |

The pyridine amide benzyl ester 15 solution in isopropyl acetate from last step was concentrated under vacuum (≦40° C. pot temperature) to a volume of 8 L and then 10 L methanol was added and the solution concentrated again to 8 L (KF<500 mg/mL). The methanol flush (temperature <50° C., 10 cm Hg) was repeated four times until all the isopropyl acetate was replaced with methanol (maximum IPAC content=50 mol % relative to benzyl ester). The resulting solution was divided into two equal portions and each subjected to the following hydrogenation condition.

To a 5-gallon stirred autoclave (Bldg. 810, A. Houck) was added the pyridine amide benzyl ester (2231 g, 5.1 mol) solution in methanol (total volume was adjusted to 17.6 L) and 27.5 mL acetic acid. To this solution was added 211.5 g 10% Pd/C. The mixture was heated to 50° C. and hydrogenated at 40 psi for 20 h.

Care should be taken when handling the methanol solution to minimize its exposure to moisture from air.

HPLC assay: same conditions as in the last step except for the solvent gradient: 0 min 100% B, 15 min A/B 10/90, 25 min A/B=20/80, 26 min 100% B. Retention time Compound B 10.5 min, the diastereomer 11.5 min, pyridine amide acid 18 min, quinine reduction products 24–25 min.

HPLC showed the de (diastereomeric excess) of Compound B was 99.6%.

After the mixture was cooled to room temperature, it was filtered through ca. 5 inches thick Solka-Floc (1 kg dried in vacuum oven, pre-washed with 4×2 L methanol) and the solid was washed with 2×2.5 L methanol. The filtration was done under nitrogen to exclude air and moisture; care was taken in handling the solutions as not to expose them to moisture from air. [Caution: Exposure of palladium catalyst over charcoal to air for several min. may start a fire.]

After the filtrate that contained Compound B was removed, water was added to wet and recover the catalyst. The filtrate was concentrated under vacuum and the total volume was adjusted to 15.3 L.

This solution was heated to reflux under nitrogen and 20 L acetonitrile was added while the solution was at reflux. The solution was seeded with 0.6 g of Compound B and another 5 L acetonitrile was added. The mixture was then stirred for 1 h without heating during which time the temperature dropped from 61 ° C. to 52° C.

White needle shaped crystals precipitated out after the 5 L acetonitrile was added.

Another 25 L acetonitrile (KF=200 mcg/ml) was added slowly (30 min) without heating during which time the temperature dropped from 52° C. to 37° C.

The mixture was stirred at room temperature overnight and then filtered (KF=1.51 mg/mL). The solid was washed with 6 L acetonitrile. The solid was dried in vacuo (50° C., 10 cm Hg) overnight to give Compound B as a white, fluffy solid.

The solid Compound B was 99.8% de. No other impurity peak was observed by HPLC.

| | |
|---|---|
| CFA: | white, bulky solid |
| X-ray: | Xtal similar to prev. |
| HPLC area %: | 99.9% |
| | no impurities >0.1% |
| Titration (HClO$_4$): | 99.9% |
| Titration (HCl): | 99.5% |
| UV: | no maxima at 200–350 nm |
| KF: | 0.2% |
| GC: | 0.02% hexanes |
| | <0.01% ethyl acetate |
| ROI: | 0.03% |
| Heavy Metal: | <10 ppm |
| Palladium: | <5 ppm |
| Nickel: | <5 ppm |
| Microscopy: | anisotropic needles |
| Particle size (avg): | 50 ± 36 μm, 95% <127 μm |
| Particle size (range): | 15–260 μm |
| Color: | 4, A% × 1000 at 440 nm |
| | (c = 1.0, H$_2$O) |
| Nephlos: | 1.3 ntu (c = 1.0, H$_2$O) |
| pH: | 7.7 (c = 1.0, H$_2$O) |
| $[\alpha]_{405}$: | −56.8° (c = 1.0, H$_2$O) |
| Purity As-Is: | 99.7% (LC-KF) |

While the invention has been described and illustrated with reference to certain preferred embodiments thereof, those skilled in the art will appreciate that various changes, modifications and substitutions can be made therein without departing from the spirit and scope of the invention. It is intended, therefore, that the invention be limited only by the scope of the claims which follow and that such claims be interpreted as broadly as is reasonable.

What is claimed is:

1. A process for forming an amide product comprising reacting a carboxylic acid and an amine, in the presence of a coupling reagent selected from EDC, DCC or diisopropylcarbodiimide and an additive, in a bi-phasic mixture of water and an organic solvent selected from isopropyl acetate, methyl t-butyl ether or toluene.

2. The process of claim 1, comprising the additional step of isolating the amide product.

3. The process of claim 1, wherein the coupling reagent is EDC.

4. The process of claim 1, wherein the organic solvent is isopropyl acetate.

5. The process of claim 1, wherein the additive is selected from the group consisting of 2-hydroxypyridine N-oxide, 1-hydroxybenzotriazole, N-hydroxysuccinimide, 1-hydroxy-7-azabenzotriazole and endo-N-hydroxy-5-norbornene-2,3-dicarboximide.

6. The process of claim 5, wherein the additive is 2-hydroxypyridine-N-oxide.

7. The process of claim 1, wherein said acid and said amine are protected amino acids.

8. The process of claim 7, wherein said acid is a protected amino acid selected from valine or phenylglycine.

9. The process of claim 1, carried out at a temperature range of about 0° to 5° C.

\* \* \* \* \*